United States Patent
Knebel et al.

(10) Patent No.: US 6,639,099 B1
(45) Date of Patent: Oct. 28, 2003

(54) PROCESS FOR SYNTHESIS OF DI(METH) ACRYLIC ACID ESTERS

(75) Inventors: Joachim Knebel, Alsbach-Haehnlein (DE); Joachim Carl, Seeheim-Jugenheim (DE); Guenter Graeff, Alsbach-Haehnlein (DE); Andrea Wittkowski, Gross-Umstadt (DE)

(73) Assignee: Roehm GmbH & Co. KG, Darmstadt (DE)

( * ) Notice: Subject to any disclaimer, the term of this patent is extended or adjusted under 35 U.S.C. 154(b) by 237 days.

(21) Appl. No.: 09/644,557

(22) Filed: Aug. 24, 2000

(30) Foreign Application Priority Data

Aug. 27, 1999 (DE) .......................... 199 40 622

(51) Int. Cl.$^7$ .............................................. C07C 67/02
(52) U.S. Cl. ..................................................... 560/217
(58) Field of Search ........................................ 560/217

(56) References Cited

U.S. PATENT DOCUMENTS 5,856,611 A    1/1999  Schlaefer et al.

FOREIGN PATENT DOCUMENTS

| DE | 28 05 702 |   | 8/1978 |
| EP | 0 236 994 |   | 9/1987 |
| GB | 2194944   | * | 3/1988 |

* cited by examiner

*Primary Examiner*—Paul J. Killos
(74) *Attorney, Agent, or Firm*—Oblon, Spivak, McClelland, Maier & Neustadt, P.C.

(57) ABSTRACT

A process for the synthesis and recovery of di(meth)acrylic acid esters at a high degree of purity. Di(meth)acrylic acid esters are produced by transesterfication of (meth)acrylic acid esters of $C_1$ to $C_4$ alcohols with 1,n-diols (where $n \geq 3$) in the presence of a zirconium catalyst that comprises a chelate of zirconium with a 1,3-dicarbonyl compound. These catalysts can be readily separated or removed from the reaction mixture by precipitation with phosphoric acid, thus providing a convenient and inexpensive method of producing a di(meth)acrylic acid ester with a reduced level of zirconium.

20 Claims, No Drawings

PROCESS FOR SYNTHESIS OF DI(METH) ACRYLIC ACID ESTERS

BACKGROUND OF THE INVENTION

1. Field of the Invention

The present invention is directed to processes for the synthesis of di(meth)acrylic acid esters by transesterification, which permit the recovery of esters that are free of high levels of undesirable contaminants such as zirconium. Preferred processes involve the transesterification of (meth)acrylic acid esters of $C_1$ to $C_4$ alcohols with 1,n-diols (where $n \geq 3$) in the presence of chelates of metal compounds as catalysts. Most preferably, chelates of zirconium with 1,3-dicarbonyl compounds are employed as the catalytic metal compounds.

2. Description of the Related Art

Di(meth)acrylic acid esters are generally obtained by the catalyzed transesterification of (meth)acrylic acid esters. Conventional metal catalysts for this transesterification are widely known among those skilled in the art. For instance, alkali metal catalysts such as lithium and calcium hydroxide are used, as described, for example, in German Unexamined Applications DE-OS 3423441 and 3423443. However, the use of these basic catalysts may lead to undesireable side reactions such as the Michael addition, which diminish both the purity and yield of the desired di-esters.

Zirconium complexes may also be used for catalysis of reactions between the esters and alcohols. Since these catalysts are neutral these complexes provide extremely high conversions and high purity of the products. A further advantage of such catalysts is that the alcohols do not have to be dried prior to transesterification. Such catalysts are described in German Unexamined Application DE-OS 2805702 and European Patent EP 0236994 B1. Zirconium catalysts may also be formed in situ. For example, FR A 2747675 describes a process for transesterification of (meth)acrylates in which zirconium catalysts are formed in situ.

Whether formed in situ or merely added to a reaction mixture, it is desireable to remove such catalysts as completely as possible after transesterification to provide a non-turbid product free of highly reactive zirconium catalysts. Di-ester products free of highly reactive zirconium catalysts are more conveniently used in subsequent reactions because they do not risk introducing undesireable effects associated with presence of these highly reactive catalysts. Accordingly, it is desireable to separate zirconium-containing catalysts from the di(meth)acrylic acid esters produced by transesterification prior to sale.

Prior methods for removing these catalysts required complex, expensive and inconvenient separation steps. For instance, separating the catalyst required hydrolysis and centrifugation, or in many cases distillation to obtain non-turbid products which had the purity required for numerous applications.

BRIEF DESCRIPTION OF THE INVENTION

An object of the present invention is to provide an inexpensive and convenient process of obtaining di(meth)acrylic acid esters in highly pure form. The present invention thus provides processes for synthesis of di(meth)acrylic acid esters by transesterification of (meth)acrylic acid esters of $C_1$ to $C_4$ alcohols with 1,n-diols (where $n \geq 3$) in the presence of metal compounds as catalysts. Preferably, chelates of zirconium with 1,3-dicarbonyl compounds are used as the metal compound. These processes produce di(meth)acrylic acid esters inexpensively and in highly pure form.

Another object of the invention is to provide a process in which the catalyst can be separated from the transesterification reaction product without energy-intensive distillation. The inventors have found that this may be achieved by precipitating the metal catalyst with phosphoric acid after transesterification. The resulting precipitate can be conveniently separated from the ester-containing reaction mixture without distillation. Accordingly, a process is provided for the synthesis of di(meth)acrylic acid esters by transesterification of (meth)acrylic acid esters of $C_1$ to $C_4$ alcohols with 1,n-diols, where $n \geq 3$, in the presence of metal compounds as catalysts, wherein chelates of zirconium with 1,3-dicarbonyl compounds are used as the metal compound. This process provides the desired di(meth)acrylic acid esters inexpensively in highly pure form without significant amounts of contaminating zirconium compounds which can interfere with subsequent chemical reactions.

Other advantages of the claimed invention include:

The inventive processes lead to extremely high conversions and high purity of the products.

The 1,n-diols used, where $n \geq 3$, do not have to be dried before they are used.

Inexpensive zirconium compounds can be used in the process, since the catalyst can be synthesized in situ by addition of 1,3-dicarbonyl compounds.

After the zirconium compounds precipitated by phosphoric acid have been separated, it is no longer necessary to purify the end product by distillation.

Products free of turbidity are obtained by the inventive process.

The notation di(meth)acrylic acid esters includes diesters of methacrylic acid, acrylic acid and mixtures of the two acids.

Di(meth)acrylic acid esters that can be synthesized in the scope of the present invention may be generally represented by the formula:

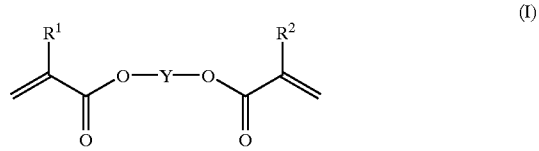

(I)

where $R^1$ and $R^2$ can be the same or different and denote a hydrogen or a methyl group, Y denotes a divalent link group, wherein the two (meth)acrylic acid groups are separated by at least 3 carbon atoms. These link groups are derived from the 1,n-diols used for transesterification.

Examples of particularly preferred link group "Y" are straight-chain, branched or cyclic alkyl groups, which can be saturated or unsaturated, such as propyl, butyl, pentyl, hexyl, cyclopentyl, cyclohexyl, pentenyl as well as polyether glycols. Link groups can contain reactive groups, examples of which include halogen-containing groups, epoxy groups, aromatic and heteroaromatic groups as well as thiol groups.

Usable (meth)acrylic acid esters of $C_1$ to $C_4$ alcohols within the scope of the invention may be represented by the formula

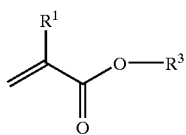 (II)

where

R¹ is hydrogen or a methyl group and R³ is an alkyl group with 1 to 4 carbon atoms.

Examples of alkyl groups with 1 to 4 carbon atoms are methyl, ethyl, n-propyl, isopropyl, n-butyl, isobutyl and tert-butyl. These groups can be unsubstituted or substituted. Either acrylic acid esters or methacrylic acid esters, or mixtures of both can be used in the transesterification.

Commercially available (meth)acrylic acid esters can be used in the inventive process with methyl acrylate and methyl methacrylate being preferred, as these substances are particularly inexpensive. Furthermore, the methanol liberated during the transesterification of these compounds can be easily removed from the reaction mixture by distillation, allowing very high conversions to be achieved.

1,n-Diols (where n≧3), include in particular compounds of the formula:

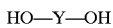 (III)

where Y has the same meaning as in formula I.

The preferred 1,n-diols include among others alkoxyalkanediols, alkenoxyalkanediols, alkenediols, glycols, polyether glycols, phenoxyalkanediols, alkylphenoxyalkanediols, phenylalkanediols, alkylphenylalkanediols, alkylmorpholinoalkanediols, alkylpiperidinoalkanediols, pyridylalkanediols, and haloalkanediols.

Preferred 1,n-diols include 1,3-propanediol, n-butane-1,3-diol, 2-methyl-1,3-propanediol, neopentyl glycol (2,2-dimethyl-1,3-propanediol), 1,4-butanediol, triethylene glycol and polyethylene glycol 400. Most preferrably the 1,n-diol is characterized in that n=3,4or 6.

The 1,n-diols can be used alone or in the form of mixtures. In general they are commercially available, and their synthesis is widely known among those skilled in the art.

The chelate complex compounds of zirconium with 1,3-dicarbonyl compounds used as catalysts in the transesterification are well known to the person skilled in the art.

The 1,3-dicarbonyl compounds that can be used with particular success in the scope of the invention include among others acetoacetic esters, acetylacetonate, 2,4-hexanedionate, 3,5-heptanedionate, 3-methylacetylacetonate, 3-phenylacetylacetonate, 4,4,4-trifluoro-1-phenyl- 1,3-butanedionate, 2,2,6,6-tetramethyl-3,5-heptanedionate, 1,1,1-trifluoro-5,5-dimethyl-2,4-hexanedionate, 1,1,1 -trifluoro-2,4-pentanedionate and dibenzoylmethane. Acetylacetone is especially preferred.

The synthesis of zirconium chelates from 1,3-dicarbonyls and zirconium compounds as well as the use of the same is described, for example, in Houben-Weyl, "Methods of Organic Chemistry" [in German], 4th Edition, Vol. VI/2, 1963, pages 53–55 and 58 to 61, and also in A. E. Martell and M. Calvin, "The Chemistry of Metal Chelate Compounds" [in German](1958).

The inventors of the present invention have made the surprising discovery that catalytically active zirconium complexes can be synthesized in situ by addition to the reagents of inexpensive zirconium compounds such as tetrabutoxyzirconium and the 1,3-diketones described hereinabove, especially acetylacetonate.

Zirconium acetylacetonate is the most preferred catalytic compound for use in conjunction with the present invention.

A single type of zirconium catalyst can be used in the inventive process or alternatively mixture of different types catalysts may be used. The proportions of catalysts used for transesterification range from 0.01 to 10 mol%, preferably from 0.05 to 10 mol%, relative to one mole of 1,n-diols.

The (meth)acrylic acid esters of formula (II) are used particularly advantageously in proportions ranging from 2 to 20 mole, especially from 3 to 12 mole, per 1 mole of 1,n-diol.

Polymerization inhibitors may be used during transesterification to prevent undesired polymerization of the (meth)acrylates. These compounds, for instance, hydroquinones, hydroquinone ethers such as hydroquinone monomethyl ether, di-tert-butylpyrocatechol, phenothiazine, p-phenylenediamine, Methylene Blue or sterically hindered phenols are widely known among those skilled in the art. These compounds can be used individually or as mixtures and are generally commercially available. The proportion of inhibitors individually or as a mixture can generally range from 0.01 to 0.5% (w/w) relative to the weight of the entire reaction mixture.

Oxygen may also be used as an inhibitor. For instance, air containing oxygen may be introduced in a proportion such that the content in the gas phase above the reaction mixture remains below the explosion limit. Proportions ranging from 0.1 to 1 liter per hour per mole of 1,n-diol are especially preferred for this purpose.

The transesterification can take place at normal pressure, negative pressure or positive pressure. The reaction temperatures can be chosen within a wide range and generally depend on the pressure used. Advantageous temperatures range, for example, from 30 to 150° C., especially from 50 to 130° C. and most preferably of all from 70 to 120° C.

Transesterification can be performed either continuously or batchwise. The inventive process can be performed in bulk, that is without using a further solvent. However, if desired, an inert solvent may be used. Examples of inert solvents include benzene, toluene, n-hexane, cyclohexane and methyl isobutyl ketone (MIBK), and methyl ethyl ketone (MEK), among others.

In a particularly expedient version of the inventive transesterification, all components, such as the 1,n-diol, the (meth)acrylic acid ester and the catalyst are mixed, after which this reaction mixture is heated to boiling. At this stage any water contained in the alcohol is first separated azeotropically with the starting (meth)acrylic acid ester. Thereafter the liberated $C_1$ to $C_4$ alcohol is removed from the reaction mixture by distillation, if possible as an azeotrope with that (meth)acrylic acid ester.

Reaction times depend on the chosen parameters, for example on pressure and temperature, on the reagents such as (meth)acrylic acid ester and 1,n-diol, and on the catalyst. In general, however, they range from 1 to 12 hours, preferably from 3 to 8 hours. The appended examples provide further information relating to reaction times for the person skilled in the art.

According to the present invention, the zirconium catalyst is separated from the mixture by addition of phosphoric acid after transesterification. The phosphoric acid can be mixed into the reaction mixture in pure form or as a solution. Addition of the phosphoric acid as an aqueous solution is particularly advantageous. The concentration of the aqueous solution can range, for example, from 0.5 to 90 wt %. The concentration also depends in particular on the 1,n-diol compound used, as can be inferred from the examples. The proportion of phosphoric acid used depends both on the zirconium compound used and on the 1,n-diol used. In general, it ranges from 0.5 to 2 moles per mole of zirconium compound to be precipitated.

A precipitate forms due to the addition of phosphoric acid. This precipitate can be separated from the reaction mixture by any method known to the person skilled in the art. Such methods include centrifuging, decanting, distillation and filtration among others. Filtration is especially preferred by virtue of its convenience and economy.

After the precipitate has been separated, the di(meth) acrylates obtained by the inventive transesterification generally exhibit, without purification by distillation, a zirconium content of less than about 1.5 ppm, preferably less than 0.7 ppm and most preferably of all less than 0.1 ppm, measured as the metal.

Depending on application, the di(meth)acrylic acid esters obtained in this way can be used without further purification. Low concentrations of residual 1,n-diol generally do not interfere with the subsequent polymerization reactions, and so conversions are substantially higher than 90% are usually achieved. The di(meth)acrylic acid esters are frequently used together with the acrylic starting substances, and so residues of these reagents do not have to be separated.

In this connection the obtained reaction mixtures are clear or substantially nonturbid after the catalyst has been precipitated by the phosphoric acid.

For special uses, however, the products obtained by the present process can also be purified by any method widely known among those skilled in the art.

The present invention will be described in detail hereinafter with reference to examples and comparison examples, which are to be regarded as non-limiting. The values in per cent relate to the total weight unless otherwise noted.

EXAMPLE 1

In an apparatus equipped with a 1-liter three-necked flask with mechanical stirrer, air inlet and top-mounted packed column (30 cm long, packed with 6 mm Raschig rings) as well as column head and reflux divider there were placed 67.5 g of 1,3-propanediol and 532 g of methyl methacrylate (MMA). To prevent undesired polymerization, 500 ppm of hydroquinone monomethyl ether was added. While air was being based in, the reaction mixture was heated to boiling. A resulting MMA-water azeotrope, which formed because of the use of moist starting materials, was distilled off until the head temperature stabilized (at about 100° C.) and clear MMA was passing over.

The reaction mixture was cooled to about 90° C., and the MMA distilled off as an azeotrope was replaced by fresh. 6 g (1% of the relative weight of the reagents) of zirconium acelylacetonate was added to the mixture. The reaction mixture was then reheated to boiling, and the MMA methanol azeotrope formed was removed from the reaction mixture by distillation. In the process the head temperature rose from 65 to about 99° C., ultimately reaching the boiling point of pure MMA. After 6 hours the reaction had ceased. At that point in time only pure MMA was still passing over. The reaction mixture was cooled, after which 25 ml of 10% phosphoric acid (aqueous solution) was added to the mixture, whereupon the zirconium catalyst precipitated out. The formed precipitate was separated by filtration, and excess MMA was removed from the mixture under vacuum.

The mixture was then analyzed by gas chromatography. The yield was 140 g. According to GC analysis, the end product contained 94.2% of 1,3-propanediol dimethacrylate,
5.2% of 1,3-propanediol monomethacrylate and
0.2% of 1,3-propanediol.

EXAMPLE 2

Example 1 hereinabove was substantially repeated, except that 78.4 g of 1,3-butanediol and 522 g of MMA were used as reagents. This mixture was stabilized with 200 ppm of hydroquinone monomethyl ether. The reaction lasted for 8 hours.

After the end of transesterification, the catalyst was precipitated with 19 ml of 1% phosphoric acid. The yield was 157 g. The end product contained 98.6% of 1,3-butanediol dimethacrylate and 0.17% of 1,3-butanediol monomethacrylate according to GC analysis. The zirconium concentration determined by atomic absorption spectroscopy (AAS) was found to be lower than 0.1 ppm.

EXAMPLE 3

Example 1 hereinabove was substantially repeated, except that 78.3 g of 2-methyl-1,3-propanediol and 522 g of MMA were used as reagents. This mixture was stabilized with 200 ppm of hydroquinone monomethyl ether. The reaction lasted for 8 hours.

After the end of transesterification, the catalyst was precipitated with 25 ml of 10% phosphoric acid. The yield was 175 g. The end product contained 98.6% of 2-methyl-1,3-propanediol dimethacrylate and 0.08% of MMA according to GC analysis.

EXAMPLE 4

Example 1 hereinabove was substantially repeated, except that 88.4 g of neopentyl glycol and 510 g of MMA were used as reagents. This mixture was stabilized with 200 ppm of hydroquinone monomethyl ether. The reaction lasted for 5 hours.

After the end of transesterification, the catalyst was precipitated with 25 ml of 10% phosphoric acid. The yield was 190 g. The end product contained 97.5% of neopentyl glycol dimethacrylate and 1.2% of MMA according to GC analysis.

EXAMPLE 5

Example 1 hereinabove was substantially repeated, except that 78.4 g of 1,4-butanediol and 522 g of MMA were used as reagents. This mixture was stabilized with 200 ppm of hydroquinone monomethyl ether. The reaction lasted for 4 hours.

After the end of transesterification, the catalyst was precipitated with 25 ml of 10% phosphoric acid. The yield was 177 g. The end product contained 99% of 1,4-butanediol dimethacrylate, 0.14% of 1,4-butanediol monomethacrylate, 0.09% of 1,4-butanediol and 0.23% of MMA according to GC analysis. The zirconium concentration was lower than 0.1 ppm according to AAS.

EXAMPLE 6

Example 1 hereinabove was substantially repeated, except that 560 g of polyethylene glycol 200 and 1500 of MMA, placed in a 4-liter three-necked flask, were used as reagents. This mixture was stabilized with 250 ppm of hydroquinone monomethyl ether. The quantity of zirconium acetylacetonate used was 25 g (1% relative to the reagents). The reaction lasted for 7 hours.

After the end of transesterification, the catalyst was precipitated with 100 ml of 10% phosphoric acid. The yield was 860 g. The end product contained 96.8% of polyethylene glycol 200 dimethacrylate, 1% of polyethylene glycol 200 monomethacrylate and 0.8% of MMA according to GC analysis.

EXAMPLE 7

Example 1 hereinabove was substantially repeated, except that 70 g of polyethylene glycol 200 and 238 g of MMA were used as reagents. The quantity of zirconium acetylacetonate used was 3 g (0.5% relative to the reagents). This mixture was stabilized with 250 ppm of hydroquinone monomethyl ether. Water was not removed from the reaction mixture during this transesterification. The reaction lasted for 6 hours.

After the end of transesterification, the catalyst was precipitated with 12.5 ml of 10% phosphoric acid. The yield was 107 g. The end product contained 96.7% of polyethylene glycol 200 dimethacrylate, 0.6% of polyethylene glycol 200 monomethacrylate and 1.3% of MMA according to GC analysis.

EXAMPLE 8

Example 1 hereinabove was substantially repeated, except that 600 g of triethylene glycol and 1800 g of MMA, placed in a 4-liter three-necked flask, were used as reagents. This mixture was stabilized with 1000 ppm of hydroquinone monomethyl ether and 250 ppm of 2,4-bis(tert-butyl)-p-cresol. The quantity of zirconium acetylacetonate used was 24 g (1% relative to the reagents). The reaction lasted for 6 hours.

After the end of transesterification, the catalyst was precipitated with 97 ml of 10% phosphoric acid. The yield was 1070 g. The end product contained 96.5% of triethylene glycol dimethacrylate, 1.12% of triethylene glycol monomethacrylate and 1% of MMA according to CC analysis. The zirconium concentration was 0.6 ppm according to AAS.

EXAMPLE 9

Example 1 hereinabove was substantially repeated, except that 100 g of polyethylene glycol 400 and 200 g of MMA, placed in a 500 ml three-necked flask, were used as reagents. This mixture was stabilized with 500 ppm of hydroquinone monomethyl ether and 250 ppm of 2,4-bis(tert-butyl)-p-cresol. The quantity of zirconium acetylacetonate used was 3 g (1% the relative weight of the reagents). The reaction lasted for 3.5 hours.

After the end of transesterification, the catalyst was precipitated with 12.5 ml of 10% phosphoric acid. The yield was 119 g. The end product contained 96.7% of polyethylene glycol 400 dimethacrylate and 0.07% of polyethylene glycol 400 monometliacrylate according to GC analysis. The zirconium concentration was 1.3 ppm according to AAS.

EXAMPLE 10

Example 1 hereinabove was substantially repeated, except that 78.4 g of 1,4-butanediol and 522 g of MMA were used as reagents. This mixture was stabilized with 120 ppm of hydroquinone monomethyl ether and 3 mg of 2,2,6,6-tetramethylpiperidyl-N-oxyl. To this composition there was added 2.9 g (6.15 mmol) of a 70% solution of tetra-n-propyl zirconate in n-propanol, whereupon a precipitate was formed. After addition of 2.5 g (25 mmol) of freshly distilled acetylacetone, the previously formed precipitate dissolved, after which the composition was heated to boiling temperature. The reaction lasted for 2 hours. Highly volatile compounds such as excess MMA were then separated under vacuum (1 mbar).

After the end of transesterification, the catalyst was precipitated with 0.83 ml of 85% phosphoric acid at room temperature. The yield was 185 g. The end product contained 98.6% of 1,4-butanediol dimethacrylate, 0.032% of 1,4-butanediol monomethacrylate, 0.6% of acetylacetone and 0.015% of MMA according to GC analysis.

COMPARATIVE EXAMPLE 1

Example 1 hereinabove was substantially repeated, except that 62 g of ethylene glycol and 600 g of MMA were used as reagents. The quantity of zirconium acetylacetonate used was 6.62 g (1% the relative weight of the reagents). This mixture was stabilized with 70 ppm of hydroquinone monomethyl ether, 40 ppm of N,N'-diphenyl-p-phenylenediamine and 10 ppm of 2,2,6,6-tetramethyl-4-hydroxypiperidine-N-oxyl. After 5.5 hours the reaction was discontinued, since no methanol had been formed.

COMPARATIVE EXAMPLE 2

Example 1 hereinabove was substantially repeated, except that 140 g (0.7 mol) of polyethylene glycol 200 and 477 g (4.77 mol) of MMA were used as reagents. The quantity of zirconium acetylacetonate used was 6.2 g (1% the relative weight of the reagents). This mixture was stabilized with 0.059 g (250 ppm relative to the reagents) of hydroquinone monomethyl ether and 5.9 mg (25 ppm relative to the reagents) of 2,2,6,6-tetramethyl-4-hydroxypiperidine-N-oxyl. Water was not removed from the reaction mixture during this transesterification. The reaction lasted for 5.5 hours.

After the end of transesterification, the catalyst was precipitated with 12.5 ml of 10% urea solution at room temperature, after which the precipitate was separated by filtration. The yield was 228 g. The end product contained 96.9% of polyethylene glycol 200 dimethacrylate and 1.07% of polyethylene glycol 200 monomethacrylate according to GC analysis. The product had a zirconium concentration of 43 ppm.

Modifications and Other Embodiments

Various modifications and variations of the described process and concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the chemical or chemical engineering arts or related fields are intended to be within the scope of the following claims.

Incorporation by Reference

Each reference, patent application or patent publication cited by or referred to in this disclosure is incorporated by reference in its entirety. Any patent document to which this application claims priority is also incorporated by reference in its entirety. Specifically, the foreign priority document which is corresponding German Patent Application 19940622.7, filed Aug. 27, 1999 is hereby incorporated by reference.

What is claimed is:

1. A process for the synthesis of di(meth)acrylic acid esters comprising:
   transesterification of
   a (meth)acrylic acid ester of a $C_1$ to $C_4$ alcohol with an 1,n-diol, where $n \geq 3$,
   in the presence of a zirconium catalyst comprising a chelate of zirconium with a 1,3-dicarbonyl compound; and
   separating said zirconium catalyst from transesterified di(meth)acrylic acid esters by precipitation with phosphoric acid.

2. The process of claim 1, wherein the zirconium catalyst is synthesized in situ from at least one zirconium compound and at least one 1,3-dicarbonyl compound.

3. The process of claim 2, wherein said zirconium compound is tetrabutoxyzirconium and said 1,3 dicarbonyl compound is acetylacetonate.

4. The process of claim 1, wherein after precipitation the di(meth)acrylic acid ester fraction has a zirconium content of less than 1.5 ppm, measured as the metal.

5. The process of claim 4, wherein the di(meth)acrylic acid ester fraction a zirconium content of less than 0.7 ppm, measured as the metal.

6. The process of claim 5, wherein the di(meth)acrylic acid ester fraction has a zirconium content of less than 0.1 ppm, measured as the metal.

7. The process of claim 1, comprising the use of at least one zirconium catalyst in a proportion of from 0.01 to 10 mol%, relative to one mole of 1,n-diols.

8. The process of claim 1, comprising the use of at least one zirconium catalyst in a proportion of from 0.05 to 10 mol%, relative to one mole of 1,n-diols.

9. The process of claim 1, wherein transesterification is performed in the presence of zirconium acetylacetonate.

10. The process of claim 1, wherein methyl methacrylate or methyl acrylate is reacted with a 1,n-diol, where n=3, 4 or 6.

11. The process of claim 1, wherein 2 to 20 mole of (meth)acrylic acid ester per 1 mole of 1,n-diol is used.

12. The process of claim 1, wherein the liberated alkanol of the (meth)acrylic acid ester is removed continuously from the reaction mixture during the reaction.

13. The process of claim 1, wherein the reaction is performed in the presence of a polymerization inhibitor.

14. The process of claim 13, wherein said polymerization inhibitor is selected from the group consisting of a: hydroquinone, hydroquinone ether, hydroquinone monomethyl ether, di-tert-butylpyrocatechol, phenothiazine, p-phenylenediamine, Methylene Blue, and a sterically hindered phenol.

15. The process of claim 1, wherein the reaction is performed in the presence of atmospheric oxygen.

16. The process of claim 1, wherein said (meth)acrylic acid ester is selected from the group consisting of methyl acrylate and methyl methacrylate.

17. The process of claim 1, wherein said 1,n-diol is selected from the group consisting of an: alkoxyalkanediol, alkenoxyalkanediol, alkenediol, glycol, polyether glycol, alkanediol, phenoxyalkanediol, alkylphenoxyalkanediol, phenylalkanediol, alkylphenylalkanediol, alkylmorpholinoalkanediol, alkylpiperidinoalkanediol, pyridylalkanediol, and haloalkanediol.

18. The process of claim 1, wherein said 1,n-diol is selected from the group consisting of: 1,3-propanediol, n-butane-1,3-diol, 2-methyl-1,3-propanediol, neopentyl glycol (2,2-dimethyl- 1,3-propanediol), 1,4-butanediol, triethylene glycol and polyethylene glycol 400.

19. The process of claim 1, wherein said 1,3-dicarbonyl compound is selected from the group consisting of: an acetoacetic ester, acetylacetonate, 2,4-hexanedionate, 3,5-heptanedionate, 3-methylacetylacetonate, 3-phenylacetylacetonate, 4,4,4-trifluoro-1-phenyl-1,3-butanedionate, 2,2,6,6-tetramethyl-3,5-heptanedionate, 1,1,1-trifluoro-5,5-dimethyl-2,4-hexanedionate, 1,1,1-trifluoro-2,4-pentanedionate and dibenzoylmethane.

20. A di(meth)acrylic acid ester composition which is produced by the process of claim 1 and which has a zirconium content in the range of 1.5 ppm or less.

* * * * *